(12) United States Patent
Kim et al.

(10) Patent No.: US 11,278,713 B2
(45) Date of Patent: Mar. 22, 2022

(54) NEURAL ELECTRODE AND MANUFACTURING METHOD THEREOF

(71) Applicant: ELECTRONICS AND TELECOMMUNICATIONS RESEARCH INSTITUTE, Daejeon (KR)

(72) Inventors: Yong Hee Kim, Daejeon (KR); Sang Don Jung, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 318 days.

(21) Appl. No.: 16/000,763

(22) Filed: Jun. 5, 2018

(65) Prior Publication Data

US 2018/0345005 A1 Dec. 6, 2018

(30) Foreign Application Priority Data

Jun. 5, 2017 (KR) ........................ 10-2017-0069845

(51) Int. Cl.
*A61N 1/04* (2006.01)
*A61N 1/05* (2006.01)
*A61B 5/24* (2021.01)
*A61N 1/36* (2006.01)

(52) U.S. Cl.
CPC .............. *A61N 1/0472* (2013.01); *A61B 5/24* (2021.01); *A61N 1/0496* (2013.01); *A61N 1/05* (2013.01); *A61B 2562/0209* (2013.01); *A61N 1/36125* (2013.01)

(58) Field of Classification Search
CPC ...... A61N 1/0472; A61N 1/0496; A61N 1/05; A61N 1/36125; A61B 5/04001; A61B 2562/0209
See application file for complete search history.

(56) References Cited

U.S. PATENT DOCUMENTS

| 5,632,770 A | * | 5/1997 | Schaldach | .............. | A61B 5/283 |
| | | | | | 607/122 |
| 2004/0220652 A1 | | 11/2004 | Zhou et al. | | |
| 2010/0273051 A1 | | 10/2010 | Choi et al. | | |

(Continued)

FOREIGN PATENT DOCUMENTS

| KR | 20100058220 | 6/2010 |
| KR | 20100117403 A | 11/2010 |

(Continued)

OTHER PUBLICATIONS

Zeng et al.("Electrodeposited Iridium Oxide on Platinum Nanocones for Improving Neural Stimulation Microelectrodes," Electrochimica Acta 237 (2017) 152-159 (Year: 2017).*

(Continued)

*Primary Examiner* — Nathan J Jenness

(57) ABSTRACT

Disclosed are a neural electrode and a method of manufacturing the electrode, more particularly, a neural electrode includes a porous nanostructure; and an iridium oxide layer formed on the porous nanostructure and a method of manufacturing the neural electrode, improving an electrode efficiency by increasing a charge injection limit capacity and the like.

5 Claims, 7 Drawing Sheets

(56) References Cited

U.S. PATENT DOCUMENTS

| | | | |
|---|---|---|---|
| 2014/0336739 A1* | 11/2014 | Lotfi | A61N 1/0551 607/116 |
| 2015/0112180 A1 | 4/2015 | Kim et al. | |
| 2016/0258070 A1 | 9/2016 | Kim et al. | |

FOREIGN PATENT DOCUMENTS

| | | |
|---|---|---|
| KR | 1020160107527 A | 9/2016 |
| WO | WO2011075480 | 6/2011 |

OTHER PUBLICATIONS

Yamagiwa et al. "Layer-by-layer assembled nanorough iridium-oxide/platinum-black for low-voltage microscale electrode neurostimulation," Sensors and Actuators B 206(2015) 205-211 (Year: 2015).*

Kim et al. In vitro extracellular recording and stimulation performance of nanoporous gold-modified multi-electrode arrays 2015 J. Neural Eng. 12 066029 (Year: 2015).*

Cogan, et al., "Sputtered Iridium Oxide Films for Neural Stimulation Electrodes," Journal of Biomedical Materials Research, 2009, vol. 89B (2), pp. 353-361.

Kim, et al., "In Vitro Extracellular Recording and Stimulation Performance of Nanoporous Gold-Modified Multi-Electrode Arrays," J. Nerual Eng., 2105, vol. 12 (6), pp. 10.

Kim, et al., "Iridium Oxide-Electrodeposited Nanoporous Gold Multielectrode Array with Enhanced Stimulus Efficacy," Nano Lett., 216, vol. 16 (11), pp. 7163-7168.

Negi, et al., "Neural Electrode Degradation from Continuous Electrical Stimulation: Comparison of Sputtered and Activated Iridium Oxide," J. Neurosci. Methods, 2010, vol. 186 (1), pp. 8-17.

Seker, et al., "The Fabrication of Low-Impedance Nanoporous Gold Multiple-Electrode Arrays for Neural Electrophysiology Studies," Nanotechnology, 2010, vol. 21 (12), pp. 7.

Zhengxu, et al., "Activated Iridium Oxide Films Fabricated by Asymmetric Pulses for Electrical Neural Microstimulation and Recording," Electrochemistry Communications, 2008, vol. 10 (5), pp. 778-782.

* cited by examiner

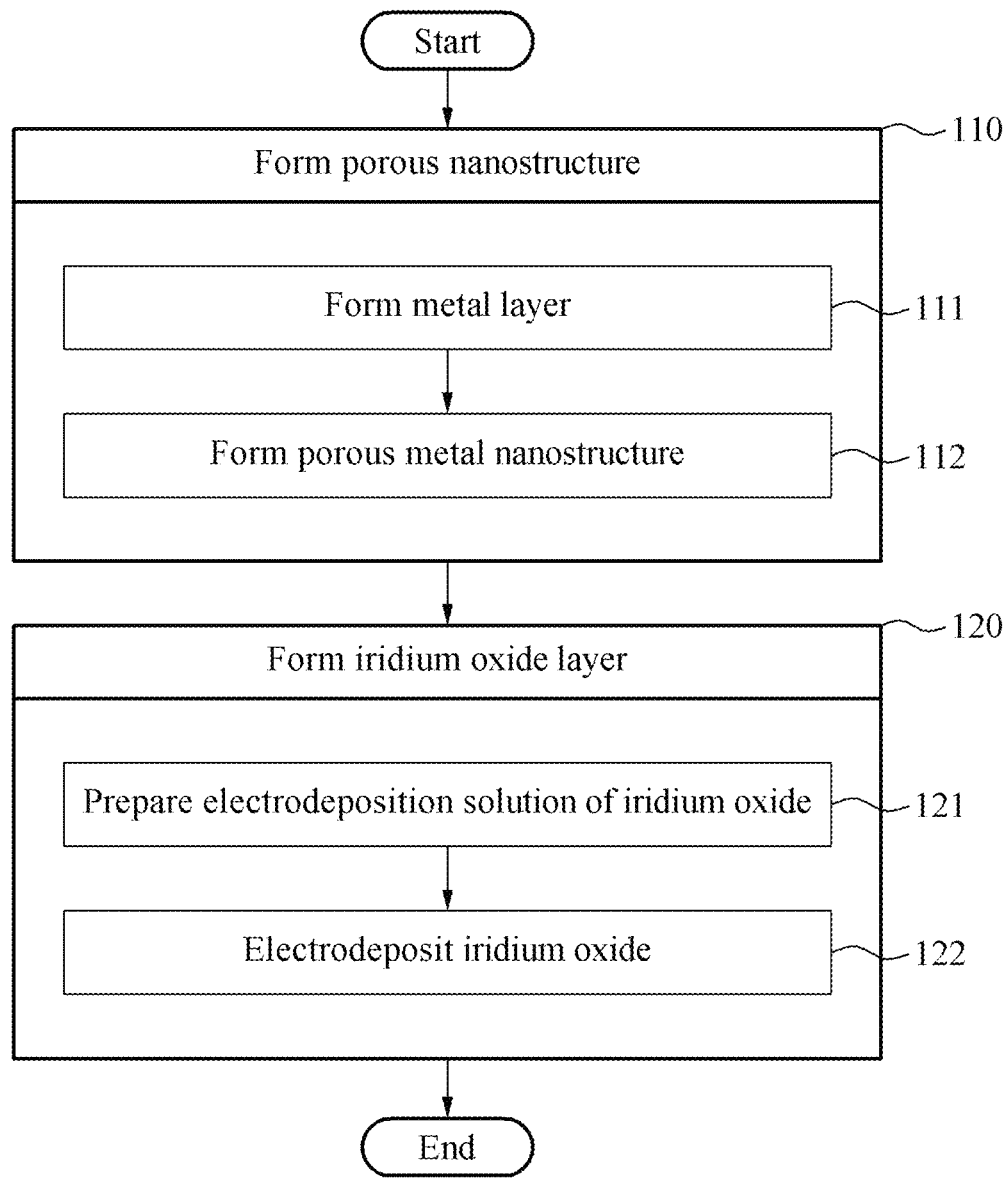

NEURAL ELECTRODE AND MANUFACTURING METHOD THEREOF

CROSS-REFERENCE TO RELATED APPLICATION(S)

This application claims the priority benefit of Korean Patent Application No. 10-2017-0069845 filed on Jun. 5, 2017, in the Korean Intellectual Property Office, the disclosure of which is incorporated herein by reference for all purposes.

BACKGROUND

1. Field

One or more example embodiments relate to a neural electrode and a method of manufacturing the neural electrode.

2. Description of Related Art

In terms of materials used for a neural electrode, research for the development of a third-generation type electrode of which a surface is modified to a nanostructure is actively being conducted based on the first-generation type electrode manufactured with a metal line using platinum, gold, tungsten, and iridium and the second-generation type electrode, such as a semiconductor electrode and a multiarray electrode.

To accurately verify a neural state, it is necessary to record a neural signal based on a neuron unit. Accordingly, an electrode needs to become as small in size as a neuron, for example, about 10 micrometers (μm). To maintain an effective signal measurement sensitivity and keep the electrode small, it is necessary to increase a surface area per unit area of the electrode. To achieve this, attempts have been made at surface modification using a nanomaterial and the like.

Charge injection limit values of platinum (Pt), TiN, and iridium oxide that are widely used as materials for a neural electrode are 0.05 to 0.3 $mC/cm^2$, 0.55 $mC/cm^2$, and 1 to 5.3 $mC/cm^2$, respectively. Iridium oxide has a relatively high charge injection limit value; however, an iridium oxide thin film becomes as much as a few micrometers (μm) thick during a process.

A neural electrode using gold as part of a structure is excellent in terms of biocompatibility; however, gold has a charge injection limit value of about 1 $mC/cm^2$ and a higher charge injection limit value is required for smooth stimulation.

SUMMARY

At least one example embodiment provides a neural electrode having an excellent signal measurement sensitivity and an enhanced charge injection capability.

At least one example embodiment also provides a method of manufacturing the neural electrode constructed as above.

The objects to be solved by the present disclosure are not limited thereto, and other objects not described herein may be clearly understood by one of ordinary skill in the art from the following description.

According to an aspect of at least one example embodiment, there is provided a neural electrode including a porous nanostructure and an iridium oxide layer formed on the porous nanostructure.

The porous nanostructure may include a pore with a size of 1 nanometer (nm) or more.

The porous nanostructure may include gold (Au), platinum (Pt), or an alloy of Au and Pt.

The porous nanostructure may have a porosity of 30% to 80%.

The iridium oxide layer may have a thickness of 1 nm to 50 nm.

The neural electrode may be a neural electrode for an electrical stimulation.

According to another aspect of at least one example embodiment, there is provided a method of manufacturing a neural electrode including forming a porous nanostructure and forming an iridium oxide layer on the porous nanostructure.

The forming of the porous nanostructure may include forming a metal layer on at least a portion of a substrate and forming a porous metal nanostructure by etching the metal layer.

The metal layer may be formed with a thickness of 100 nm or more.

The forming of the metal layer may use an electrodeposition method, a deposition method, a powder coating method, or a sol-gel method.

The metal layer may include a first metal and a second metal, and a mass ratio of the first metal to the second metal may be 1:9 to 5:5.

The first metal may include Au, Pt, or both of Au and Pt, and the second metal may include silver (Ag), copper (Cu), or both of Ag and Cu.

The forming of the porous metal nanostructure by etching the metal layer may include forming the porous metal nanostructure of a first metal by selectively etching the metal layer that includes a second metal.

The forming of the iridium oxide layer on the porous nanostructure may include preparing an electrodeposition solution of iridium oxide and immersing the porous nanostructure in the electrodeposition solution and electrodepositing iridium oxide on the porous nanostructure.

The electrodepositing of the iridium oxide may use a cyclic voltammetry (CV) method, a constant current (CC) method, or a potentiostatic method.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects, features, and advantages of the invention will become apparent and more readily appreciated from the following description of example embodiments, taken in conjunction with the accompanying drawings of which:

FIG. 1 is a flowchart illustrating a method of manufacturing an electrode according to an example embodiment;

DETAILED DESCRIPTION

Figure 2A:
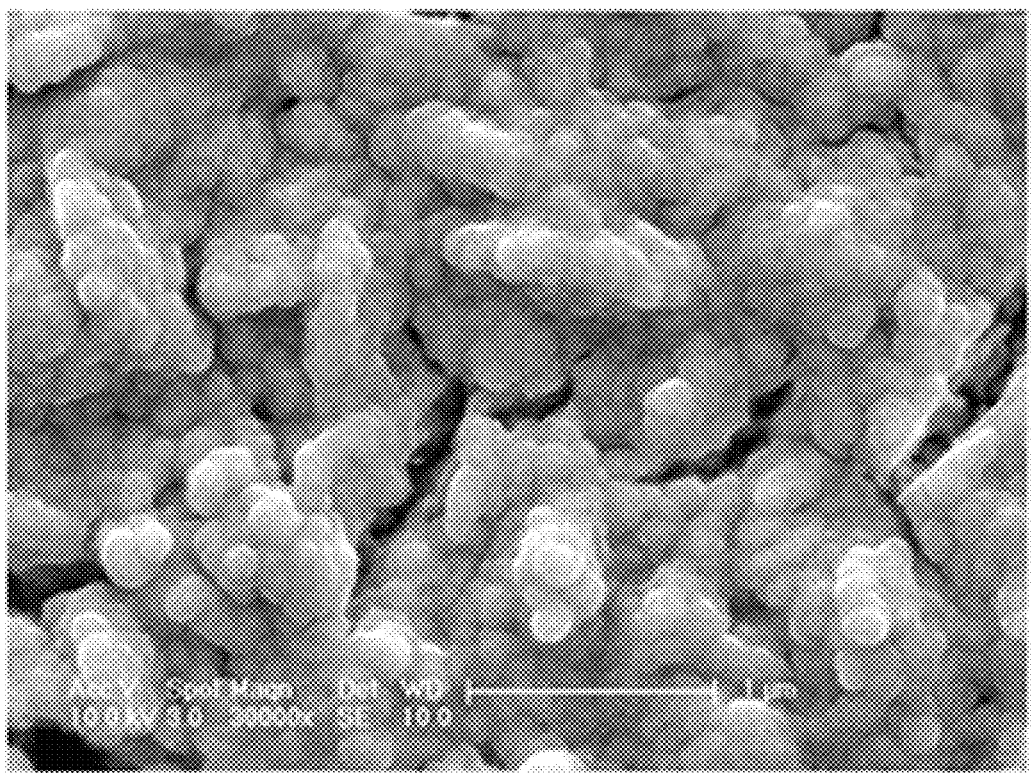
FIGS. 2A and 2B illustrate examples of a scanning electron microscope (SEM) image of a neural electrode manufactured according to an example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

The following detailed structural or functional description of example embodiments is provided as an example only and various alterations and modifications may be made to the example embodiments. Accordingly, the example embodiments are not construed as being limited to the disclosure and should be understood to include all changes, equivalents, and replacements within the technical scope of the disclosure.

According to an example embodiment, there is provided a neural electrode that may provide an improved electrode performance through a wide surface area by a porous nanostructure and excellent electrical properties, such as a charge storage capacity and a charge injection limit by oxide.

According to an example embodiment, the neural electrode may be in a hierarchical structure including a porous nanostructure and an iridium oxide layer formed on the porous nanostructure.

According to an example embodiment, the porous nanostructure may provide a significantly wide surface area compared to that of an existing deposited metal electrode or a metal nanoparticle and reduce an electrochemical impedance of the neural electrode. For example, the porous nanostructure may include gold (Au), platinum (Pt), or an alloy of Au and Pt. Desirably, the porous nanostructure may include Au based on a biocompatibility and an in vivo safety.

According to an example embodiment, the porous nanostructure may have a porosity within a range of 30% to 80% or 50% to 80%. If the porosity of the porous nanostructure is included within the above range, the surface area of the neural electrode may significantly increase. In addition, a wide surface area may be maintained although a thickness of the iridium oxide layer becomes relatively thin.

According to an example embodiment, modifying a surface of the porous nanostructure with the iridium oxide layer may improve electrical properties, such as a charge storage capacity and a charge injection limit of the neural electrode, and improve a charge injection efficiency of the neural electrode. Thus, a cell, such as a neuron, may be smoothly stimulated without damaging the cell.

For example, the iridium oxide layer may be formed with a thickness within a range of 1 nanometer (nm) to 50 nm or 1 nm to 20 nm. If the thickness of the iridium oxide layer is in the above range, the wide surface by the porous nanostructure may be maintained, and the excellent charge injection limit value may be provided.

According to an example embodiment, an electrochemical impedance of the neural electrode may be 10,000Ω or less. Such a relatively low electrochemical impedance value may be suitable for the neural electrode and prevent a degradation of a signal measurement sensitivity by thermal or electrical noise.

According to an example embodiment, the neural electrode may be a neural electrode array on which a plurality of porous nanostructures is formed.

According to an example embodiment, the neural electrode may be applied as an electrode for an electrical stimulation or an electrode for measuring in vivo and/or in vitro neural signal to record a stimulation and a neural signal. The neural electrode may have an excellent signal sensitivity and an improved charge injection efficiency, thereby achieving an excellent electrical stimulation efficiency.

According to an example embodiment, there is provided a method of manufacturing the neural electrode constructed as above. Since the iridium oxide layer is electrodeposited using an electrochemical method, a thickness of the iridium oxide layer may be easily adjusted, and a performance of the neural electrode may be improved with a relatively low production process cost.

FIG. 1 is a flowchart illustrating a method of manufacturing an electrode according to an example embodiment. Referring to FIG. 1, the method may include operation 110 of forming a porous nanostructure and operation 120 of forming an iridium oxide layer.

According to an example embodiment, operation 110 may include operation 111 of forming a metal layer and operation 112 of forming a porous metal nanostructure.

Operation 111 may be an operation of forming the metal layer on at least a portion of one side or both sides of a substrate. For example, the substrate may be a target electrode. Any type of electrodes applicable to the neural electrode may be used for the target electrode. For example, the target electrode may include at least one of platinum (Pt), gold (Au), tungsten (W), and iridium (Ir).

For example, the metal layer formed in operation 111 may include a first metal and a second metal. Here, the first metal may include, for example, Au, Pt, or both of Au and Pt. The second metal may include a metal to which a chemical etching is applicable. For example, the second metal may include silver (Ag), copper (Cu), or both of Ag, and Cu. For example, the first metal and the second metal may be in nanocrystal grain forms of the respective corresponding metals or nanocrystal grain forms of an alloy thereof.

For example, a mass ratio of the first metal to the second metal may be within a range of 1:9 to 5:5. If the mass ratio is included in the range, a structurally stable porous nanostructure having a relatively high porosity may be formed by selective etching the metal layer that includes the second metal.

In operation 111, the metal layer with a thickness of, for example, 100 nanometers (nm) or more, 100 nm to 2000 micrometers (μm), or 100 nm to 1000 nm may be formed.

In operation 111, the metal layer may be formed using, for example, an electrodeposition method.

Here, the electrodeposition method relates to coating an electrode with a target material to be electrodeposited. In an electrodeposition solution in which the target material is dissolved in a solvent, the target material is moved to an anode or a cathode and is used to coat the cathode or the anode through an electrochemical reaction in the cathode or the anode.

For example, the electrodeposition method may perform an electro-co-deposition of the first metal and the second metal and may use a cyclic voltammetry (CV) method, a constant current (CC) method, or a potentiostatic method.

For example, the electrodeposition solution may include at least one of nitrate, hydrochloride, chloride, phosphate, borate, oxide, sulfonate, sulfate, stearate, myristate, acetate of each of the first metal and the second metal and a salt including a cation of a corresponding metal.

Operation 112 may be an operation of forming the porous metal nanostructure by etching at least a portion of the metal layer. For example, the porous metal nanostructure of the first metal may be formed by selectively etching the metal layer that includes the second metal through an etching process.

Here, operation 112 of forming the porous metal nanostructure may use a wet etching method.

The wet etching method relates to performing etching through a contact between a basic etching solution or an acidic etching solution and the metal layer. For example, the basic etching solution that provides hydroxyl ions is an inorganic basic solution or an organic basic solution. The basic etching solution may include at least one of lithium hydroxide (LiOH), sodium hydroxide (NaOH), potassium hydroxide (KOH), rubidium hydroxide (RbOH), caesium hydroxide (CsOH), barium hydroxide (Ba(OH)$_2$), strontium hydroxide (Sr(OH)$_2$), calcium hydroxide (Ca(OH)$_2$), copper hydroxide (Cu(OH)$_2$), iron hydroxide (Fe(OH)$_2$), ammonium hydroxide (NH$_4$OH), tetramethyl ammonium hydroxide (N(CH$_3$)$_4$OH), tetrabutylammonium hydroxide ((C$_4$H$_9$)$_4$NOH), choline hydroxide, alanine, phosphazene, histidine, imidazole, benzimidazole, purine, pyridine, pyrimidine, and methyl amine.

For example, the acidic etching solution may include at least one of phosphoric acid, sulfuric acid, acetic acid, nitric acid, hydrofluoric acid, and hydrochloric acid.

The wet etching method may control an etching amount and a porosity by controlling potentials of hydrogen (pH) of a corresponding etching solution, a type of the etching solution, an etching temperature and/or an etching time. For example, the wet etching method may be performed at a temperature of 100 degrees celsius (° C.) or less, room temperature to 90° C., room temperature to 80° C., or 50° C. to 70° C. for 1 minute (min) to 2 hours (hrs), or 2 mins to 30 mins.

In operation 112, the porous metal nanostructure may be randomly or uniformly etched or may be etched to be in various shapes, for example, a porous particle, a nanoroad, a nanoneedle, and a nanowire.

According to an example embodiment, operation 120 may be an operation of forming the iridium oxide layer on the porous nanostructure formed in operation 110. A surface of the porous nanostructure may be modified by electrodepositing the iridium oxide layer on the porous nanostructure using an electrochemical method. Also, the electrodeposition by the electrochemical method may effectively coat, at a relatively low cost, the porous nanostructure having random and various shapes with the iridium oxide layer.

Operation 120 may include operation 121 of preparing an electrodeposition solution of iridium oxide and operation 122 of electrodepositing iridium oxide.

In operation 121, the electrodeposition solution including an iridium salt, an additive, and a solvent may be prepared.

Here, the iridium salt may include at least one of, for example, a nitrate, a hydrochloride, a chloride, a phosphate, a borate, an oxide, a sulfonate, a sulfate, a stearate, a myristate, an acetate of iridium and a salt including a cation of the iridium.

The additive may include, for example, a pH regulator, an accelerator, and a surfactant, and the solvent may include, for example, hydrogen peroxide, potassium perchlorate, oxalic acid, sodium oxalate, potassium oxalate, sodium sulfate, and the like. The solvent may be water or a mixture of water and an organic solvent.

Operation 122 may be an operation of immersing the porous nanostructure in the electrodeposition solution and electrodepositing iridium oxide on the porous nanostructure. In operation 122, a coating membrane with a uniform thickness and concentration may be formed on the porous nanostructure having the random and various shapes by applying the electrochemical electrodeposition method. Also, a forming rate of the coating membrane may be fast, and a control of the thickness may be easy.

For example, in operation 122, iridium oxide may be electrodeposited at a rate of 50 millivolts per second (mV/s) or more or 100 mV/s to 200 mV/s within a voltage range of −0.9 V to 0.8 V.

Also, in operation 122, an electrodeposition may be performed during an appropriate amount of time to control the thickness of the iridium oxide layer. For example, iridium oxide may be electrodeposited using the CV method, the CC method, or the potentiostatic method for 1 min to 2 hrs or 30 mins through 1 hr.

According to an example embodiment, there is provided a neural electrode having an excellent biocompatibility and an improved signal measurement sensitivity and charge injection capability by electrodepositing iridium oxide on a surface of a porous nanostructure.

Hereinafter, the present disclosure will be described with reference to example embodiments, however, it will be apparent to those of ordinary skill in the art that various changes and modifications may be made without departing from the scope of the.

EXAMPLE (1) An Electrode Array on which an Alloy of Gold (Au)/Silver (Ag) Nanoparticles is Electrodeposited:

A 0.1 molarity (M) H$_2$SO$_4$ solution including 5 mM HAuCl$_4$ was manufactured. A neural electrode array on which Au nanoparticles were to be electrodeposited was prepared as a working electrode. An Ag/AgCl electrode in a KCl saturated solution was prepared as a reference electrode. A platinum (Pt) plate was prepared as a counter electrode. The neural electrode array on which a nanoparticle layer was formed through an electrodeposition of the Au nanoparticle was manufactured by applying a constant voltage of about −0.5 V for 10 mins. An electrolyte solution was manufactured using 50 mM KAu(CN)$_2$, 50 mM K$_2$Ag(CN)$_3$, 0.2M KCN, and 0.5M KOH. In the electrolyte solution, the neural electrode array on which the Au nanoparticles were formed was prepared as the working electrode. The Ag/AgCl electrode in the KCl saturated solution was prepared as the reference electrode, and the Pt plate was prepared as the counter electrode. The electrode array on which the alloy of Au/Ag nanoparticles was electrodeposited was manufactured by applying a constant voltage of about −0.9 V for 300 seconds (sec).

(2) Manufacturing of a Porous Au Nanostructure:

The porous Au nanostructure was manufactured by immersing the electrode array on which the alloy of Au/Ag nanoparticles was electrodeposited in a HNO$_3$ solution at a temperature of about 70 degrees celsius (° C.) for 7 mins and etching the electrode array with Ag.

Figure 2B:
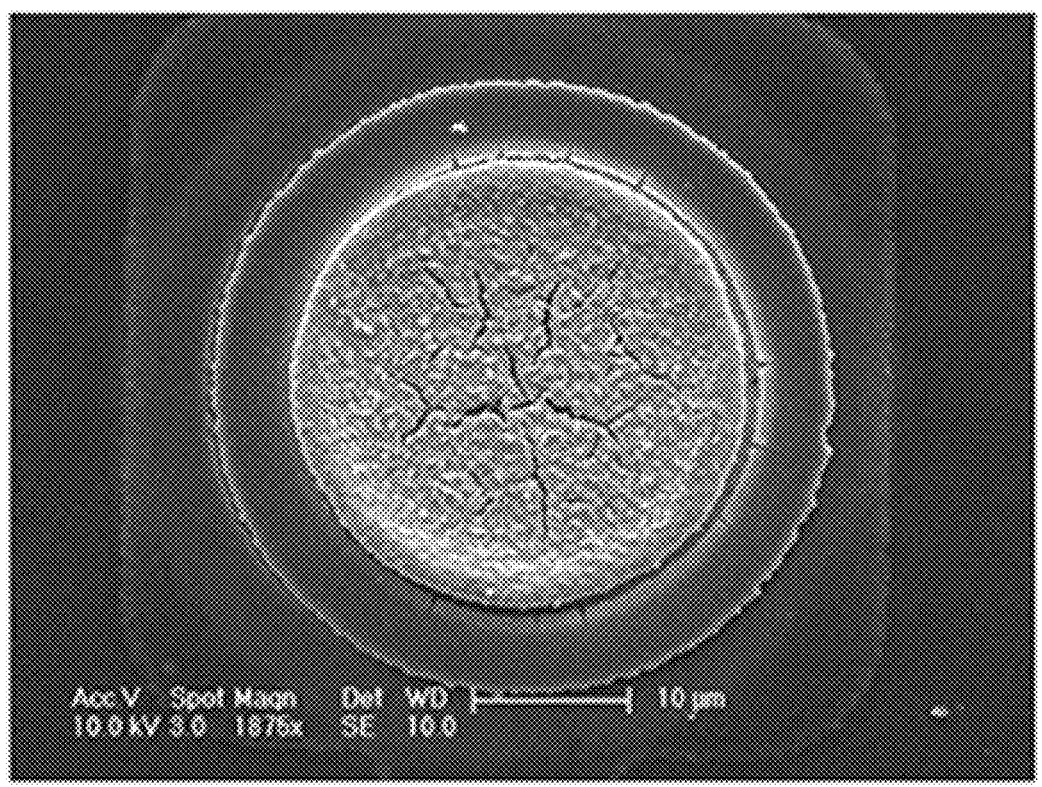
Figure 3A:
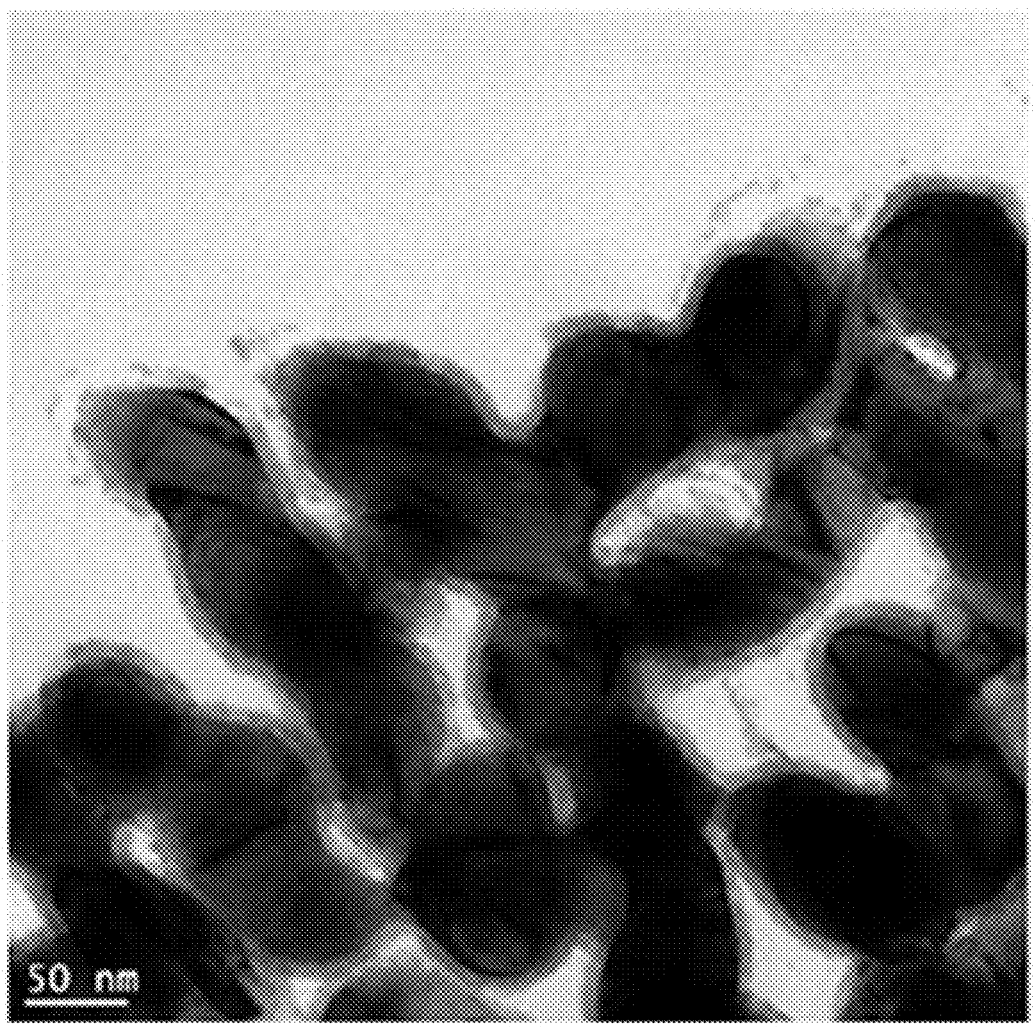
FIGS. 3A and 3B illustrate examples of a transmission electron microscope (TEM) image of a neural electrode manufactured according to an example embodiment.
Figure 3B:
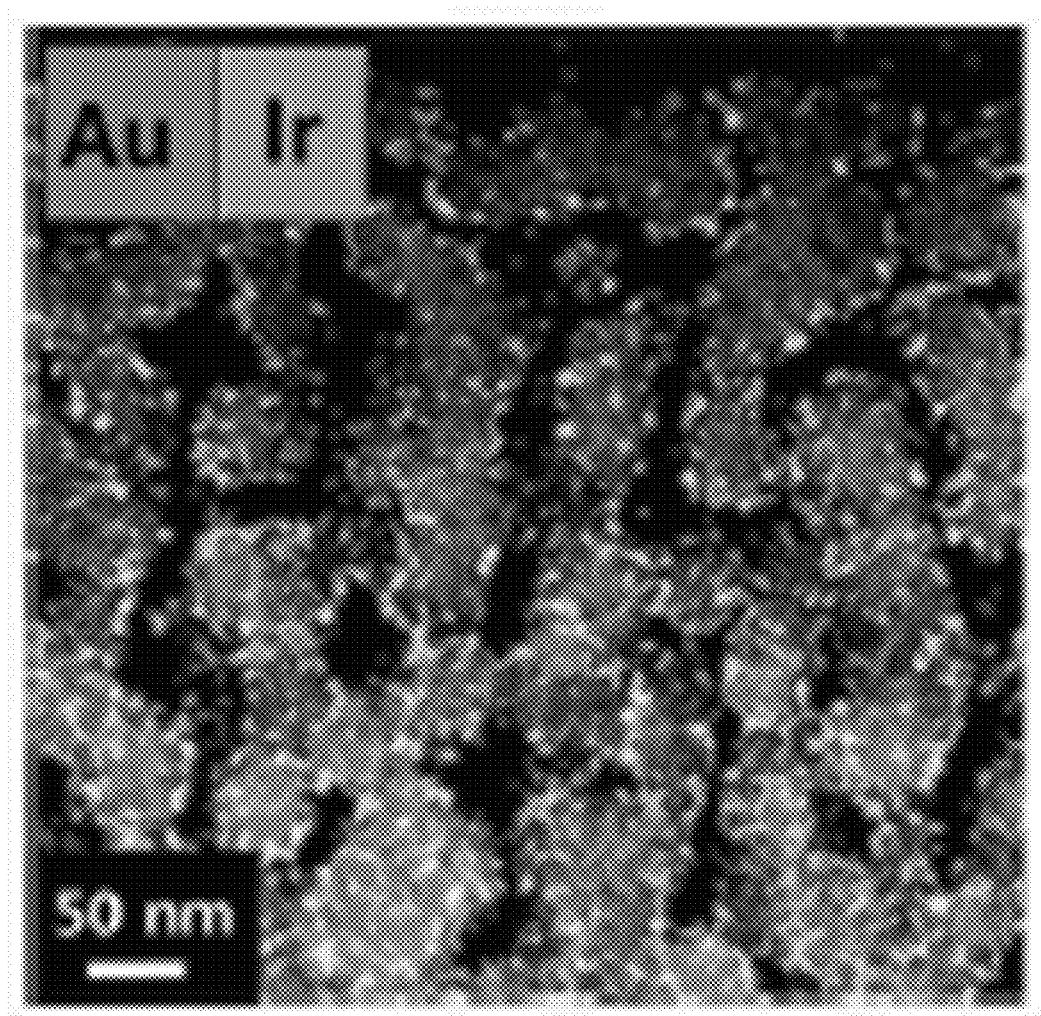

(3) Forming of an Iridium Oxide Layer:

A mixture was manufactured by dissolving about 0.07 gram (g) of iridium chloride in about 50 milliliters (ml) of water and stirring the mixture for 30 mins. About 0.5 ml of 30% hydrogen peroxide was added to the mixture, and the mixture was stirred for 5 mins. About 250 milligrams (mg) of oxalic acid was added to the mixture, and the mixture was stirred for 10 mins. An iridium oxide sol was manufactured by adding potassium perchlorate ($KClO_4$) to the mixture and adjusting pH of the mixture to be about 10.5. The iridium oxide sol of which a color changed to dark purple through a stabilization operation was used as an electrodeposition solution. An iridium oxide-porous Au nanostructure electrode was manufactured by electrodepositing the iridium oxide layer with a thickness of about 10 nm on the porous Au nanostructure at a rate of about 100 mV/S in a voltage range of −0.8 V to 0.7 V using a CV method. A scanning electron microscope (SEM) image and a transmission electron microscope (TEM) image of the manufactured iridium oxide-porous Au nanostructure electrode/a scanning transmission electron microscope-energy dispersive X-ray spectrometry (STEM-EDS) element mapping image were captured and are shown in FIGS. 2A and 2B, and FIGS. 3A and 3B. FIG. 2A illustrates an SEM image of an electrode surface, and FIG. 2B illustrates an SEM image of an entire electrode. FIG. 3A illustrates a TEM image and FIG. 3B illustrates a STEM-EDS element mapping image. Referring to FIGS. 2A and 2B, and FIGS. 3A and 3B, it can be verified that the iridium oxide layer is uniformly electrodeposited on the Au porous structure.

Comparative Example 1

An Au substrate on which iridium oxide was electrodeposited was manufactured by electrodepositing iridium oxide on the Au substrate. Comparative example 1 was performed under the same condition as that of Example.

Comparative Example 2

A porous Au nanostructure electrode on which iridium oxide was not electrodeposited was manufactured. Comparative example 2 was performed under the same condition as that of Example.

Experimental Example 1

Figure 4B:
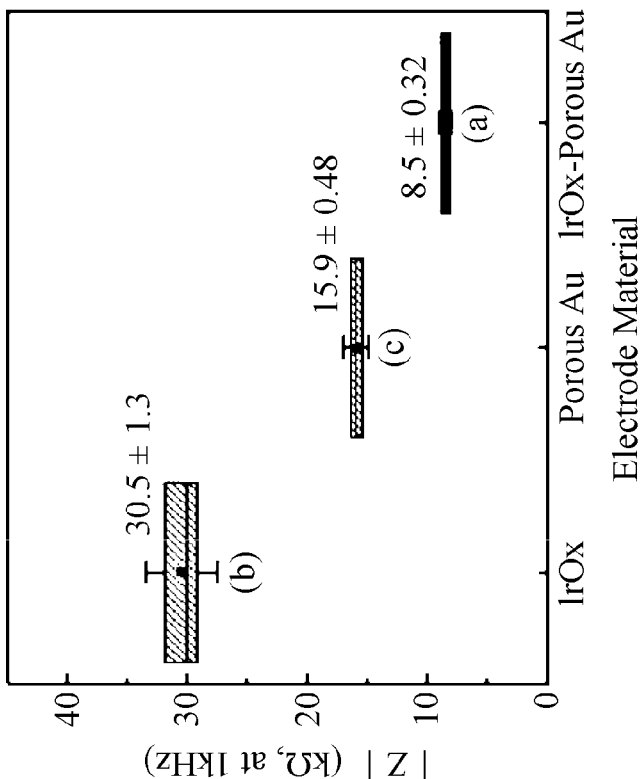
FIGS. 4A and 4B are graphs showing an electrochemical impedance measured according to Experimental example 1 of an example embodiment.
Figure 4A:
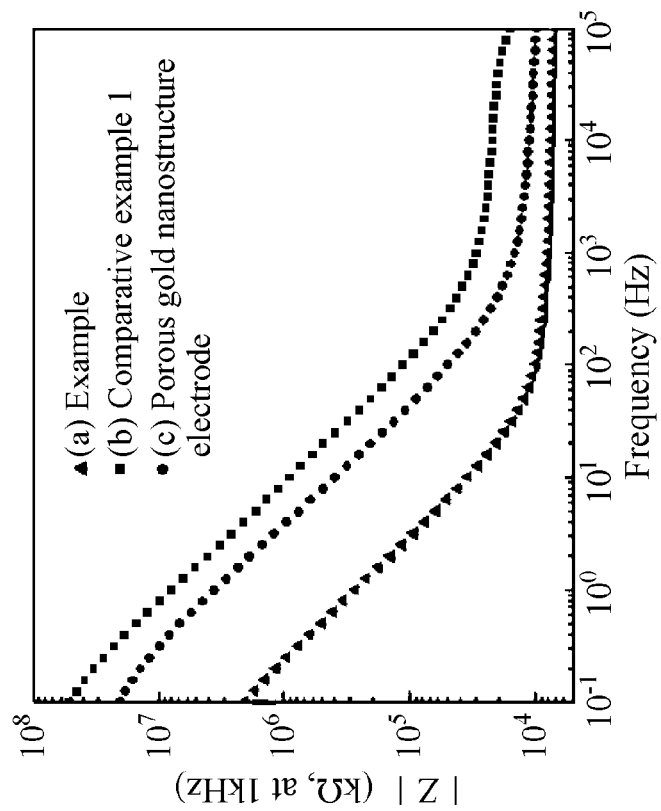

Electrochemical impedances of (a) the iridium oxide-porous Au nanostructure electrode in Example, (b) an iridium oxide-Au nanoparticle electrode manufactured in Comparative example 1, and (c) the porous Au nanostructure electrode on which iridium oxide was not electrodeposited in Comparative example 2 were measured and are represented in FIGS. 4A and 4B.

Referring to FIGS. 4A and 4B, a most significant decreases in an electrochemical impedance value can be verified as being in the iridium oxide-porous Au nanostructure electrode by the present disclosure. The electrochemical impedance may decrease due to an increase in a surface area of the iridium oxide-porous Au nanostructure electrode. Such a low electrochemical impedance may decrease thermal or electrical noise, etc., and improve a sensitivity of a measurement signal.

Experimental Example 2

Charge injection limits of (a) the iridium oxide-porous Au nanostructure electrode in Example and (b) the iridium oxide-Au nanoparticle electrode in Comparative example 1 were measured with a voltage transient and are represented in Table 1.

TABLE 1

|  | (a) | (b) |
|---|---|---|
| $mC/cm^2$ (100-cycled) | 2.3 | 0.1 |

Referring to Table 1, a value of the charge injection limit of (a) the iridium oxide-porous Au nanostructure electrode in Example is about 2.3 $mC/cm^2$. It can be verified that this value is higher than a theoretical neural damage threshold, here, ca. 1 $mC/cm^2$, and that of (b) the iridium oxide-Au nanoparticle electrode. That is, the example embodiment may provide a neural electrode having an improved charge injection efficiency by a wide surface area of a porous Au nanostructure and an excellent electrical activity of iridium oxide in the iridium oxide-porous Au nanostructure electrode.

Experimental Example 3

Figure 5:
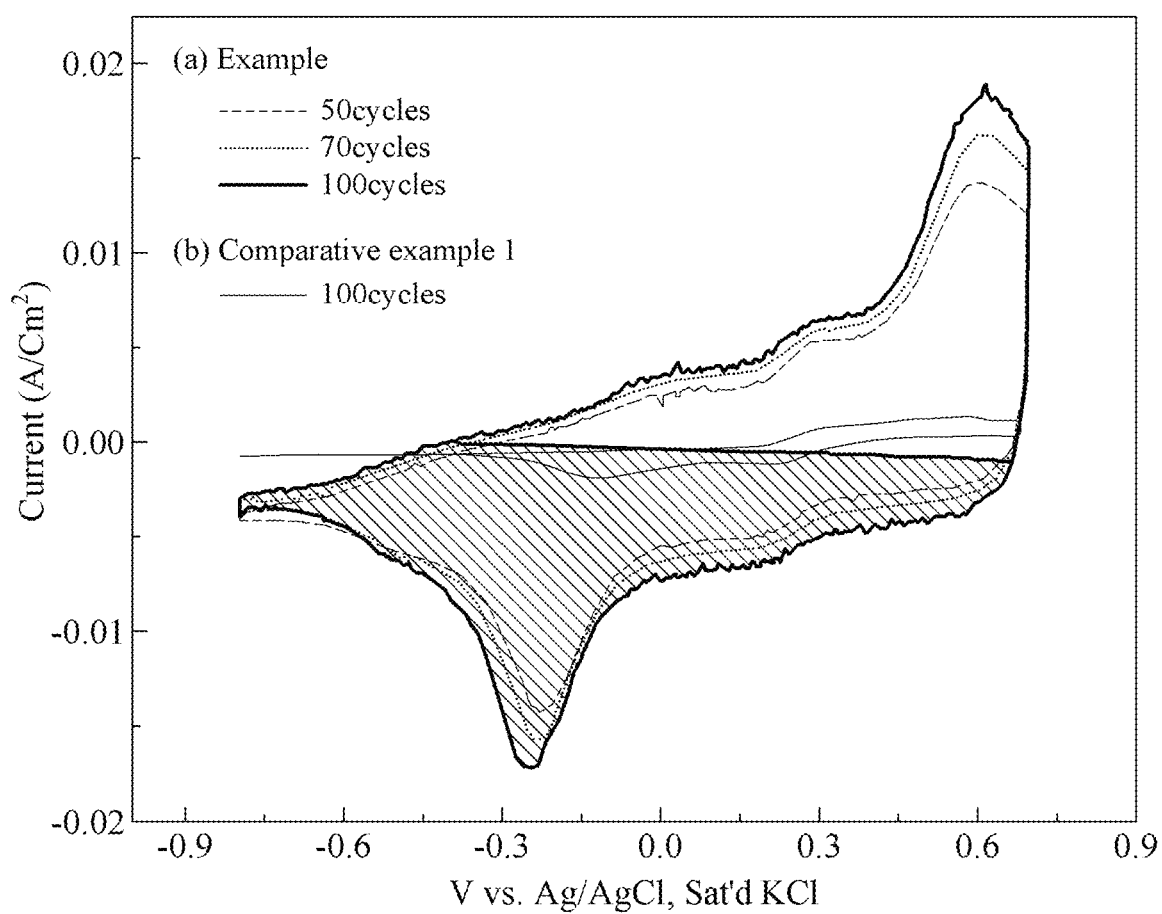
FIG. 5 is a graph showing a cyclic voltammogram (CV) measured according to Experimental example 3 of an example embodiment.

Values of CV in (a) the iridium oxide-porous Au nanostructure electrode in Example and (b) the iridium oxide-Au nanoparticle electrode in Comparative example 1 were measured and are shown in FIG. 5. Referring to FIG. 5, it can be verified that, after 100 cycles, a value of a charge storage capacity of the iridium oxide-porous Au nanostructure electrode in Example is greater than that of the iridium oxide-Au nanoparticle electrode in Comparative example 1 in a reduction current region area.

According to example embodiments, there may be provided is a neural electrode having an excellent signal sensitivity and an improved charge injection efficiency through a wide surface area by a porous nanostructure and an electrical activity based on iridium oxide.

Also, according to example embodiments, there may be provided a neural electrode that may detect a brain signal with a high sensitivity and effectively stimulate a nerve tissue since a charge injection limit capacity and the like are improved. The neural electrode may achieve an excellent biocompatibility and safety in a living body without damaging a neuron cell.

Also, according to example embodiments, there may be provided a neuron electrode that may provide wide surface area by applying a porous nanostructure. Also, since iridium oxide is electrodeposited on the porous nanostructure using an electronic chemical method, a production process cost may be saved.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A neural electrode comprising:
   a porous nanostructure; and
   an iridium oxide layer formed on the surface of the porous nanostructure,
   wherein the porous nanostructure comprises gold (Au) or an alloy of Au and platinum (Pt),
   wherein the porous nanostructure has a porosity of 30% to 80%, wherein the pores of the porous nanostructure are formed by depositing the Au or Au Pt alloy along with a third metal and removing the third metal, the Au or Au Pt alloy and the third metal forming a metal layer with a thickness of 100 nm to 2000 micrometers (μm) and including nanocrystal grain forms, wherein a mass ratio of the Au or the alloy of Au and Pt to the third metal is 1:9 to 5:5, wherein the porous nanostructure comprises a porous nanoparticle, and wherein the third metal is silver, copper or both.

2. The neural electrode of claim 1, wherein the porous nanostructure comprises a pore with a size of 1 nanometer (nm) or more.

3. The neural electrode of claim 1, wherein the porous nanostructure consists essentially of gold (Au).

4. The neural electrode of claim 1, wherein the iridium oxide layer has a thickness of 1 nm to 50 nm.

5. The neural electrode of claim 1, wherein the neural electrode is a neural electrode for an electrical stimulation.

\* \* \* \* \*